(12) United States Patent
Marcus

(10) Patent No.: US 6,432,063 B1
(45) Date of Patent: Aug. 13, 2002

(54) METHOD FOR DIRECT DIAGNOSIS AND TREATMENT OF PAIN OF MUSCULAR ORIGIN

(75) Inventor: Norman J. Marcus, New York, NY (US)

(73) Assignee: Norman Marcus Pain Institute, New York, NY (US)

( * ) Notice: Subject to any disclaimer, the term of this patent is extended or adjusted under 35 U.S.C. 154(b) by 50 days.

(21) Appl. No.: 09/593,485

(22) Filed: Jun. 14, 2000

Related U.S. Application Data

(60) Provisional application No. 60/139,110, filed on Jun. 14, 1999.

(51) Int. Cl.[7] .............................. A61B 5/05; A61N 1/18
(52) U.S. Cl. .......................................... 600/554; 607/46
(58) Field of Search ................................ 600/554, 557; 607/3, 46

(56) References Cited

U.S. PATENT DOCUMENTS

| | | | |
|---|---|---|---|
| 5,425,751 A | * | 6/1995 | Baeten et al. |
| 5,653,739 A | | 8/1997 | Maurer et al. |
| 5,938,690 A | | 8/1999 | Law et al. |
| 6,044,303 A | | 3/2000 | Agarwala et al. |

OTHER PUBLICATIONS

By D. J. Simons, "Myofascial pain syndromes due to trigger points: 1. Principles, diagnosis, and perpetuating factors", *Manual Medicine* (1985) 1:67–71.

By R. D. Gerwin, "The Clinical Assessment of Myofascial Pain" in *Handbook of pain assessment* (1992), ed. by D. C. Turk et al., The Guilford Press, New York, pp. 61–70.

By "Interrater reliability in myofascial trigger point examination", *Pain* (1997) 69:65–73.

By H. Kraus et al., "The reintroduction of an exercise program to directly treat low back pain of muscular origin", *Journal of Back and Musculoskeletal Rehabilitation* (1997) 8:95–107.

By M. B. Wyszynski, "The New York Pain Treatment Program Protocol: a structured physical therapy approach for treating the muscular components of chronic pain syndromes", *Journal of back and Musculoskeletal Rehabilitation* (1997) 8:109–123.

* cited by examiner

*Primary Examiner*—Scott M. Getzow
(74) *Attorney, Agent, or Firm*—Pennie & Edmonds LLP

(57) ABSTRACT

The present invention relates to a method for direct diagnosis and treatment of a patient with a pain of muscular origin. The method comprises: a) applying an electric stimulus to a muscle in a suspected area of pain, using a neuromuscular stimulator; b) recording the patient's response to the stimulus; c) repeating steps a) and b) in a different area with resultant decrease in discomfort; d) repeating a), b) and c) to find a point of maximal sensitivity; and e) effectively treating the point of maximum sensitivity.

5 Claims, No Drawings

METHOD FOR DIRECT DIAGNOSIS AND TREATMENT OF PAIN OF MUSCULAR ORIGIN

1. CROSS-REFERENCE TO RELATED APPLICATION

This is a non-provisional application based on provisional application Ser. No. 60/139,110 filed Jun. 14, 1999.

TABLE OF CONTENTS

1. CROSS-REFERENCE TO RELATED APPLICATION . . . 2
2. BACKGROUND OF THE INVENTION . . . 2
   2.1. Field of the Invention . . . 2
   2.2. Description of the Background Art . . . 3
3. SUMMARY OF THE INVENTION . . . 4
4. DETAILED DESCRIPTION OF THE PREFERRED EMBODIMENTS . . . 5
   4.1 Description . . . 5
   4.2. Example . . . 8
5. CLAIMS . . . 11
6. ABSTRACT . . . 12

2. BACKGROUND OF THE INVENTION

2.1. Field of the Invention

The present invention relates to a method of determining the cause of pain in a patient and then provide a specific treatment for such pain. More particularly, the present invention relates to a method of determining whether the pain is originated from the muscles of the patient and provide a specific treatment for such pain. More particularly, the present invention relates to a method of electrical stimulation which can accurately pinpoint the specific area of a muscle producing a patient's pain complaint.

2.2. Description of the Background Art

Myofascial pain syndrome can be literally interpreted to describe pain coming from muscles and connective tissue. Despite its liberal meaning in various literature, myofascial pain syndrome normally refers to a wide variety of supposed clinical entities, such as tension, weakness, stiffness, trigger points and tender points. In addition, myofascial pain syndrome can be part of the syndrome referred to as fibromyalgia.

Among the most common causes of pain seen in clinical practice, myofascial pain syndrome is characterized by myofascial trigger points. Trigger points are only one of the many causes that have been equated with myofascial pain. Even though there is no clinical procedure/criteria as to examining patients with muscle pain, many clinicians consider myofascial trigger points as tender areas of muscle that have associated point tenderness on a taught muscle band, local twitch response, referred pain, reproduction of usual pain, restricted range of motion, weakness without atrophy, and autonomic symptoms. Other clinicians believe that pain on palpation reproducing the usual pain is enough to make the diagnosis of a trigger point.

Satellite myofascial trigger points often develop in the zone of referred pain. Secondary myofascial trigger points are found in muscles in the functional motor unit affected. Once these satellite or secondary myofascial trigger points develop, they may persist, eventually referring pain to their own pain reference zones. In this way, the areas of the body involved with myofascial pain syndrome increases, eventually affecting multiple regions.

It is essential for the proper diagnosis and treatment of myofascial pain syndrome that all of the etiologies associated with pain caused by muscle and connective tissue be identified. The prior art has required skill by the clinician in the physical examination of muscle in finding the specific point in the muscle causing the pain in order to identify myofascial trigger points. Since criteria vary for the diagnosis of trigger points, interrater reliability in locating myofascial trigger points is frequently low Accuracy, consistency, stability and reproducibility of the examination technique is referred to as reliability. The agreement between two or more examiners is referred to as interrater reliability. Interrater reliability is poor when palpation is used as the identifying technique, in part due to the lack of standards as to the amount of pressure to exert when palpating a muscle.

The prior art attempts to locate or confirm myofascial trigger points using techniques more objective than palpation. Such techniques include a palpation index, handheld pressure threshold meter, electronic pressure meter attached to the fingers, thermographic measurement of heat emission and electromyographic identification.

However, these techniques are difficult to learn and use on routine patients in a limited period of time. A simple method is desired that can accurately define, diagnose and lead to the treatment of all of the causes of muscle pain, including trigger points associated with the patient's pain complaint.

Accordingly, it is an object of the present invention to provide a method for diagnosing myofascial pain syndrome with precision to enable more effective treatment of the condition.

Another object of the invention is to provide a technique for examining a patient having myofascial pain syndrome with better accuracy, consistency, stability and reproducibility of the procedure.

Yet another object is to provide a method of examining a patient having myofascial pain syndrome with a high degree of interrater reliability in locating trigger points.

Yet another object is to provide a technique for diagnosing myofascial pain syndrome in the specific area of the muscle producing pain complaint within a limited period of time.

Yet another object is to provide a diagnosis that offers a possible explanation for pain which without such diagnosis would automatically be attributed to the spine and nervous system, possibly leading to utilization of expensive and unnecessary tests and treatments including surgery.

These and other objects of the invention as well as other advantages thereof can be apprehended by reference to the following description and claims.

3. SUMMARY OF THE INVENTION

The foregoing objects are achieved according to the present invention which provides a simple method by which the physician can accurately define, diagnose, and treat specific muscle causes of a patient's pain complaint. In a preferred embodiment, electrical stimulation is used to find muscle pain emanating from trigger points.

According to a preferred embodiment of the present invention, the method comprises: (a) applying an electric stimulus to a muscle through a neuromuscular stimulator and recording the patient's response; (b) repeating step (a) in a different location with resultant decrease in discomfort; and (c) effectively treating the points of maximum sensitivity.

The method of the present invention is useful for all patients whose muscles may be the underlying cause of the pain complaint. It is particularly useful when trigger points are considered in very muscular and/or obese patients since manual palpation of these patients will frequently produce a low pressure in deep muscles. Such a low pressure is insufficient to excite a painful area in order to produce discomfort and thus prove the muscles to be causes of the patient's pain.

The present invention is useful in the treatment of pain for a variety of conditions, and in particular back pain, neck pain, shoulder pain, extremity pain, headaches, and abdominal pain.

4. DETAILED DESCRIPTION OF THE PREFERRED EMBODIMENTS 4.1 Description

A. Initial Evaluation

The process begins with an initial evaluation. The initial evaluation should produce details of a patient's activities and habits that may cause the pain. The initial evaluation is an important part of the entire diagnosis, since the ultimate goal is to eliminate factors that cause the pain. After a successful treatment is conducted, these factors would be eliminated from the patient's repertoire.

Types of such factors would be all activities involved in over-use or inappropriate use of musculature. Such inappropriate use would include the following situations: (1) engaging in athletic activities with insufficient warm-up or exercising machines that produce non-physiological positioning, (2) exercising with machines that produce unbalanced exercise routines or abrupt changes in the intensity of an exercise machine, such as changes in the use of an exercise equipment like a re-stringed a tennis racquet, (3) engaging in work position that could lead to strain of muscle groups, such as typing on a computer keyboard placed on the top of a desk rather than in a tray under the desk, looking at a computer monitor improperly positioned so that it is not directly in front of the patient and at eye level or slightly below, holding a telephone handset to the user's ear, or reading and watching television in bed. Hence, no matter what the patient's occupation or use of leisure time is, one can always discover other activities that produce repetitive strain to muscles.

The pain complaint is detailed as much as possible to determine frequently found patterns of pain involving specific muscle groups. For example, a back pain radiating down the leg is frequently thought of as coming from nerve root compression beginning in the spine. In most cases this will not be so. Therefore, whenever a pain pattern would traditionally suggest compression of nerves in the spine, one should be thinking of the typical muscle patterns that could also be producing the same symptom complex. Muscle pain will frequently be made worse by inactivity and relieved to some degree with motion of the effected muscles. The effected muscle may not produce pain when the patient only engages in minimal activity; but as soon as a greater intensity of activity is initiated, the pain may recur.

The physical examination is critical for the diagnosis of muscle pain. The examination will determine if the patient has minimal trunk muscle strength and flexibility to support themselves without discomfort. The basic test is the Kraus-Weber test, originally developed at Columbia University in the 50's. The Kraus-Weber test measures strength of abdominal muscles and hip flexors as well as back muscle extensors. It measures the flexibility of the low back, hamstrings, and calf muscles as well. The test provides us with a measure of trunk muscle tension, weakness, and stiffness. These diagnoses are all amiable to correction with Kraus' exercise program developed at Columbia University in 1954. After the Kraus-Weber test, the patient is manually examined.

The first part of the manual examination is pinching the skin in the painful area. The skin in the painful area will itself be painful in more than 50% of patients presenting with muscle pain. One should moderately forcefully pinch the patient, grabbing approximately 2 cm of skin between the thumb and forefinger, and then comparing the discomfort in that region with skin over the midriff as a reference point. When the skin is very tender, this tenderness can be eliminated with a skin rolling massage, which is a pinching, kneading, rolling massage to the area of the painful skin. These massages are given every other day and last for 15 minutes each time. They are very uncomfortable and the patient is iced to the painful skin area for approximately 8 minutes prior to the skin rolling massage. Following eight sessions of such massages, in almost all cases the skin pain is dramatically reduced or eliminated. The patient is then instructed to use a loofa sponge on the previously painful skin area in a bath or shower on a daily basis.

Muscles are then examined. The muscles are firmly palpated, comparing right to left whenever the examination is done to see if there is a significant difference between the right side and left side. This examination may demonstrate that the patient has diffuse tenderness or focal tenderness. When there is focal tenderness it may be the result of stiffness, tension, spasm or trigger points. Spraying a coolant spray such as ethyl chloride onto the muscle and asking the patient to contract and relax the muscle rhythmically for 1 or 2 minutes and spraying in between whenever the patient reports continued pain may eliminate the pain coming from tension and stiffness. It may temporarily help a muscle in spasm; but it will not relieve a trigger point.

The Marcus method states that trigger points do not develop for approximately 2 months after the initiation of pain in a particular region of the body. If a patient is treated early enough with techniques to be described below, the pain may disappear.

A confounding element in the prior art is, when one determines that a trigger point is present and if such diagnosis is made, the technique to treat the diagnosed point area or muscle. The techniques currently considered community standard, accept without question repeated injection of a muscle for weeks, months, or years. The technique of injecting that we utilize is based on the assumption that the entire muscle is dysfunctional and therefore, that when a trigger point is found, the entire muscle needs to be injected along the entire origin and insertion of that particular muscle. Because this requires extensive injecting, only one muscle is done per day. Deciding on the presence of the trigger point remains a clinical challenge.

B. Direct Diagnosis

Our unique contribution is our discovery that high voltage electrical stimulation of a suspected area will pinpoint of the muscles involved in causing the patient's pain. In the present invention, an electrical stimulus is applied to a muscle through neuromuscular stimulator. The stimulus is applied through a roving electrode that can be moved over a painful muscle until the patient reports discomfort. The electrode is then moved to another area with resultant decrease in discomfort. This process is repeated to ascertain the accuracy of the point of maximal sensitivity. Preferably the process is repeated 2 to 10 times, and preferably 3 to 4 times. This produces a reliable replication of the patient's pain and gives the treating physician the security that an injection is warranted.

With repeated stimulation to the muscle that is painful, should one find that the patient reports a decrease in pain with subsequent stimulation, then this is the area that in most cases will not require injection but will respond to additional electrical stimulation coupled with deep point massage. The uniqueness of the present invention, however, is the ability to find the spot that does not yield to electricity but consistently produces the patient's pain. No other technique in the prior art describes such a diagnostic capacity. This, coupled with the unique approach of injecting the entirety of the muscle rather than a specific point, makes this technique dramatically more effective as a diagnostic and treating regime for common pain problems such as low back pain.

Should this technique be used in its entirety, the generic term myofascial pain syndrome would become a manageable entity since specific treatments for specific aspects the syndrome could and would be applied. Since the diagnosis and treatment of muscles as a primary cause of pain heretofore was absent, patients have suffered physically, emotionally and financially by overlooking inexpensive effective techniques and utilizing inappropriate, ineffective diagnostics and treatment techniques.

The method of the present invention is illustrated by the following non-limited example.

4.2. Example

A 45-year-old female patient out of work on disability with a chief complaint of pain in the right perihip and right lower extremity with radiation into the right lateral mid calf, and also in the left buttock. Her pain is described as an intermittent shooting sensation. Sitting for more than ten minutes, walking for more than five minutes, standing in one spot, or bending over will all increase her pain.

She denies sensory loss, weakness, or sphincter changes. The pain will interrupt her sleep.

HISTORY OF PAIN: In 1996, she had the insidious onset of right low back pain and buttock pain and noted problems straightening up when she would stand up. The pain slowly began to increase in intensity and spread to involve the right lower extremity. She saw her family doctor in 1997 and was diagnosed with sciatica. She was given analgesics and muscle relaxants and had complete relief of her pain. In October of 1998, she had recurrence of pain and once again saw her internist who ordered studies and referred her to surgical consults. The medical records that were reviewed show x-rays done in October of 1998 of the LS spine which were read as degenerative disk disease at L5-S1 and an MRI done in October of 1998 of the LS spine read as L4-5 large herniated disc with right L5 nerve root displacement.

PHYSICAL EXAMINATION: Examination reveals the patient to be able to bend over to within 12" of the floor with knees together and erect and actually to lose 4" when asked to do so in a more relaxed fashion. Straight leg raising is 500 bilaterally. Tests for abdominal strength and hip flexors reveals the patient to have weakened abdominals. Examination of back muscle extensors reveals the patient to have adequate strength. She is able to walk on toes and heels. Examination of the subcutaneous tissue reveals tenderness over the right lateral thigh and over the right perihip. Examination of the musculature reveals trigger points in the right tensor fasciae latae, vastus lateralis, gluteus, and peroneus. There is also a questionable trigger point over the left gluteus. Neurologic examination reveals knee jerks and ankle jerks to be positive and symmetrical. Sensory examination is within normal limits.

IMPRESSION: 1. MYOFASCIAL PAIN SYNDROME
2. MUSCLE SPASM
3. SKIN TENDERNESS

This female patient does not have an operable lesion based on her findings on physical examination. Her history also does not suggest that her problems are related to the findings on the MRI. She does have skin and muscle pain that will totally reproduce all of her symptoms. Indeed, when cold spray is used in the course of the examination and gentle limbering exercises are done, the patient reports almost complete relief of her pain.

Considering the dramatic response to minimal intervention, the patient will be seen for baseline physical therapy evaluation to establish parameters against which future treatment can be assessed. She will then receive a gentle exercise program developed specifically for back pain that will provide her with relaxation, limbering, stretching, and strengthening. Should she still have pain after doing these exercises for approximately one month, we will then embark on a course of injections to the above noted muscles. In addition, the patient will be provided with skin rolling massage to eliminate the skin tenderness that is noted above.

She was given the Kraus exercises program which did produce increased range of motion in her low back and hips. She felt generally more limber but still had sciatica like pain. Reassessment of her muscles revealed trigger point as initially noted. Electrical stimulation of the right low back and hip girdle muscles identified the right lumbar paraspinal as being the most involved muscle. This was the first muscle to be injected and following the three days of post injection physical therapy (neuromuscular stimulation producing rhythmic contractions every 2 seconds of the injected muscle followed by limbering movements of the muscle and when pain would occur—cold spray), she had 85% relief with the first treatment and required only one more muscle injection to eliminate her muscle pain and return to work after. The use of the electrical stimulus to identify the most important muscle aided in reducing the overall length and cost of treatment.

The patient attended two weeks of treatment and was discharged pain free with an exercise program that she could do independently at home on a daily basis.

The foregoing description is only illustrative of the principle of the present invention. It is to be recognized and understood that the invention is not to be limited to the exact configuration as described herein. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A method for direct diagnosis and treatment of a patient with a pain of muscular origin comprising:
   a) applying an electric stimulus to a muscle in a suspected area of pain, using a neuromuscular stimulator;
   b) recording the patient's discomfort and/or pain response to the stimulus;
   c) repeating steps a) and b) in a different area with resultant decrease in discomfort;
   d) repeating a), b) and c) to find a point of maximal sensitivity; and
   e) effectively treating the point of maximum sensitivity.

2. The method according to claim 1, wherein steps a) through d) are repeated 2 to 10 times.

3. The method according to claim 2, wherein steps a) through d) are repeated 3 to 4 times.

4. The method according to claim 1, wherein the point of maximum sensitivity is treated by an injection of the entire muscle.

5. The method according to claim 1, wherein the point of maximum sensitivity is treated by additional electrical stimulation coupled with deep point massage.

* * * * *